United States Patent [19]

Berndt

[11] Patent Number: 4,544,273
[45] Date of Patent: Oct. 1, 1985

[54] SMOKE OPACITY METER
[75] Inventor: Dale F. Berndt, Plymouth, Minn.
[73] Assignee: Particulate Instruments, Plymouth, Minn.
[21] Appl. No.: 518,633
[22] Filed: Jul. 29, 1983
[51] Int. Cl.⁴ ............................................. G01N 21/00
[52] U.S. Cl. .................................... 356/434; 356/437; 356/438; 356/439
[58] Field of Search ................. 356/437, 438, 439, 434

[56] References Cited
U.S. PATENT DOCUMENTS
3,826,577 7/1974 Irwin ..................................... 356/438

Primary Examiner—Bernard D. Pianalto
Attorney, Agent, or Firm—Orrin M. Haugen; Thomas J. Nikolai

[57] ABSTRACT

Apparatus for controllably admitting a sample volume of engine exhaust into a bifurcated, closed-loop opacity chamber and wherein the exhaust sample is controllably directed away from the internal optics via symmetric flow inducing air guides. A pulsed light source is controllably directed through the opacity chamber and exhaust sample and the detected light is compared to a reference level so as to determine a relative measure of the sample's opacity. Attendant control circuitry permits the selected display of corresponding sample opacity and density values.

12 Claims, 8 Drawing Figures

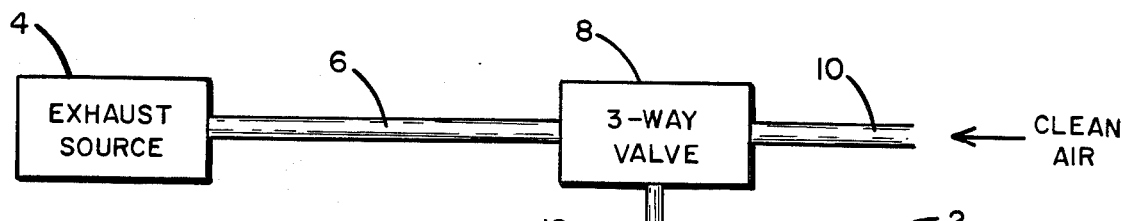
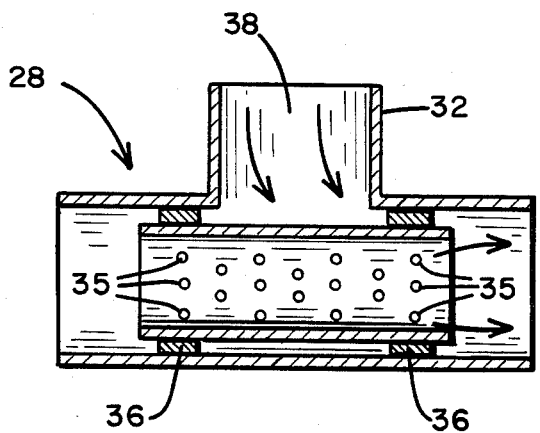
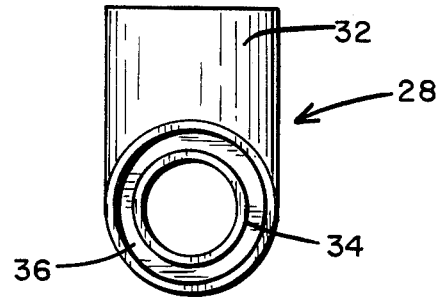
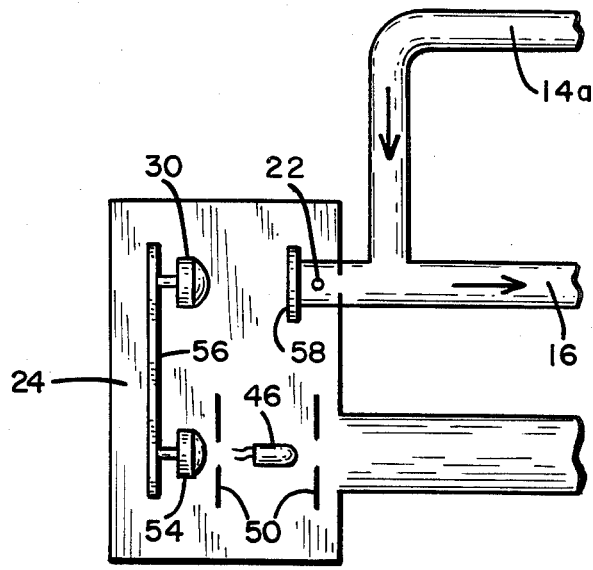

| Fig. 5b |
| Fig. 5a |

SMOKE OPACITY METER

BACKGROUND OF THE INVENTION

The present invention relates to opacity testing apparatus and in particular to apparatus for sampling the exhaust of internal combustion (i.e., diesel or gas) engines and determining the relative opacity or particulate content of the exhaust.

As exhaust emission standards are implemented by the Federal and State Governments, it becomes necessary for the truck and auto manufacturers and, in particular the engine designers to design engines that meet the emission standards. One of such standards is directed to the particulate emissions from such engines and the measure of which emissions is related to an optical percentage scale and against which the clarity or opacity of the emissions are measured. Because such standards are only of recent origin, most test equipment is only presently undergoing development, although some equipment does exist relative to monitoring smoke stacks or the like. This inventor is also aware of a previously developed system that is sold by Celesco/Berkeley and which is manufactured by Telonic Berkeley of Irvine, California for measuring engine exhaust, but which system has an optical sampling head that attaches to the exhaust pipe and whereat the opacity of the exhaust is directly and optically monitored across the exhaust outlet. Shortfalls of this equipment, however, are that it has a rather cumbersome optical sampling head which can become optically misaligned during handling in addition to which it produces large amounts of noise. This noise is superimposed on the electrically measured output signal, thus limiting the sensitivity of the equipment and producing a relatively unstable zero reference signal level.

Because of these various shortcomings and due to a desire to develop test equipment that is more compatible with efficient testing procedures, the present rack-mounted assembly was developed. This equipment essentially comprises a sampler tube for coupling a portion of the engine exhaust to a valve, whereat clean air may be alternatively admitted, such as at the end of a test run and prior to admitting the exhaust air to a closed-loop opacity chamber. The present opacity chamber, in turn, is comprised of a differentially pressurized, bifurcated path whereby the sample is divided at an input port and caused to flow into oposite ends of the sample tube and exit from an outlet port that is coupled midway therealong to an appropriate air pump. The flow is thus directed from opposite ends of the opacity chamber, towards the center, while an appropriately shaped and amplified pulsed beam of light is directed from one end and through the center of the chamber to the other end and whereat the emerging light is compared to a reference light level that is determined from the pulsed light source so as to generate a related percentage of opacity. Alternative reference light sources are further disclosed, wherein in one embodiment, a beam splitter is employed in conjunction with a reference detector; and wherein in a second embodiment, the reference detector and opacity detector are mounted in the same ambient environment, while the reference detector responsively detects the back light of the pulsed light source. The details thereof will, however, become more apparent upon reference to the following description of the present invention with respect to the following drawings.

Before referring thereto, however, it is to be recognized that the present invention is described with respect to its presently preferred embodiment and, therefore, that various modifications may be made thereto without departing from the spirit and scope of the described invention. Accordingly, the present invention is not to be limited only to that configuration disclosed hereinafter.

BRIEF DESCRIPTION OF THE DRAWINGS

FIG. 1 shows a generalized system diagram of the present apparatus.

FIG. 3a shows a detailed elevation view of the present coaxial flow Tees.

FIG. 3b shows an end view of the coaxial Tee of FIG. 3a.

FIG. 4, shows a generalized diagram of an alternative embodiment for the reference signal generator.

SUMMARY OF THE INVENTION

Figure 2:
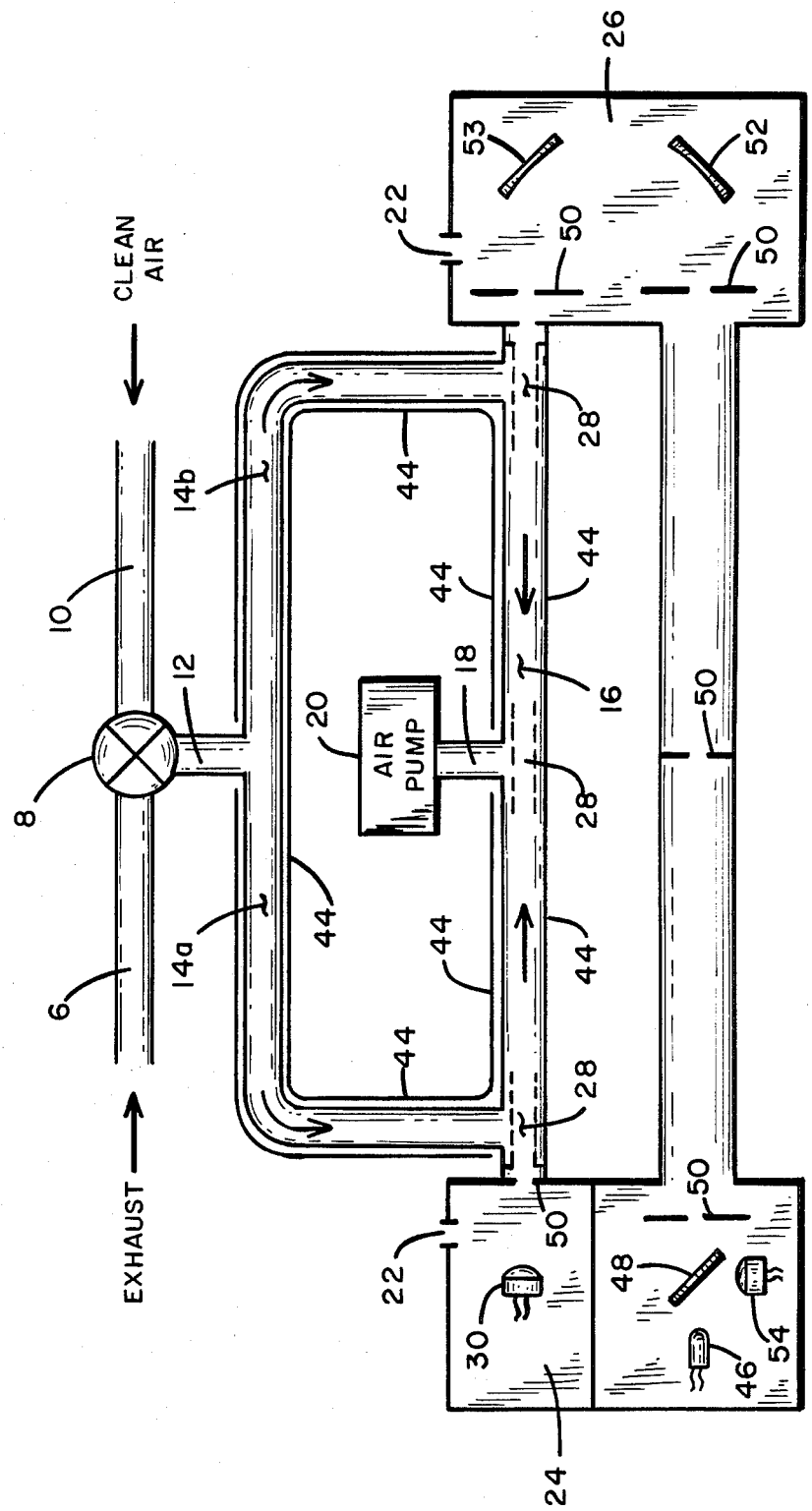
FIG. 2 shows a system diagram of the present opacity chamber relative to the generated and detected optics and sample airflow.

A smoke opacity meter wherein engine exhaust samples are admitted to a bifurcated, closed-loop opacity chamber and wherein the particulate containing sample is monitored via photo-optic detection means. The sample is further constrained to flow in the path via clean air admitting orifices in the light emitting and detecting ends of the chamber and wherein a cylindrically symmetrical air flow is achieved via coaxial flow Tees that provide for an air flow that does not introduce turbulance and thereby does not affect the light transmission measurement.

A collimated optical beam is achieved via a pulsed light source which passes through a plurality of apertures and which is amplified and focused via a concave mirror before passing through the sample tube and being detected via the detector. An optical reference is achieved at the source via a beam splitter which samples the input light so as to produce a reference signal by which the light source may be stabilized. Alternatively, an arrangement is contemplated wherein the reference detector and sample detector are mounted in a similar thermal environment and whereby the reference detector directly senses back scattered light from the light source and thereby achieves a longer term stability and calibration for the equipment.

DESCRIPTION OF THE PREFERRED EMBODIMENT

Referring to FIG. 1, a general system diagram is shown of the present apparatus relative to its mounting in a typical test system. In that regards, the present opacity meter 2 is coupled to a source of engine exhaust 4 via a sample tube 6 and which tube 6 is coupled via a coupler (not shown) that mounts to the exhaust system associated with the engine and which acts to channel a portion thereof to the present opacity meter 2. For the present embodiment, the sampler tube 6 is approximately ¼ inch inside diameter and acts to produce a continuous sample at approximately one cubic foot per minute.

The sample of exhaust is, in turn, conveyed via the sampler tube 6 to an electronically controlled three-way valve 8 that is mounted in the meter 2, even though it is presently shown external thereto. The valve 8, in turn, is coupled to a source of fresh air via a tube 10 and the meter 2 via a tube 12 and whereby a quantity of clean air may alternatively be admitted to the meter 2 such as at the end of a test run to flush the system thereby preventing against build up of particulates therein. During testing, though, the particulate containing exhaust is channeled via the valve 8 to the opacity chamber contained in meter 2. For the present embodiment, it should be noted, too, that the total length of the typical sample path for tubes 6 and 12 is kept to a minimum so as to minimize possible particulate losses within the tubes.

The tube 12, in turn, is coupled to the opacity chamber wherein the sample is appropriately channeled relative to a light source and optical detector for providing a relative measure of the opacity or amount of light that is blocked by the particulates of the exhaust sample. Thus, as particulate density increases, the associated amount of absorption and scattering of the light increases and thereby reduces the percentage of light detected. Accordingly, the present meter operates between a range of zero to 100 percent opacity and whereat the zero level is set pursuant to a sampling of the clean air of the local environment via the tube 10 before switching the three-way valve 8 so as to monitor the exhaust via the tube 6. Upon monitoring the environmental air, the zero level is set via the calibration controls of the present apparatus. From the perspective view of FIG. 1 of the present meter 2 it is to be noted that controls are appropriately provided for supplying equipment power, operating the sample pump, digital display and temperature controller and permitting the measurement of opacity, density and the integrated mass of the sample. The details of such controls will, however, become more apparent upon reference to the following drawings and the associated descriptions thereof.

Referring, therefore, to FIG. 2, a more detailed block diagram is shown of the present sampling equipment relative to the flow path of the opacity chamber the optical source and the detector circuitry. From FIG. 2, it is to be noted that as the sample is admitted to the meter 2, it is divided and caused to flow along the paths 14a and 14b before entering the extreme ends of the opacity chamber 16. Upon entering the opacity chamber 16, the sampled exhaust air is directed centrally towards the outlet port 18 via an air pump 20 coupled thereto. Thus, a pressure differential exists between the inlet tube 12 and the outlet port 18 so as to cause the sample to flow in the above described manner.

Additionally, small air inlet ports 22 are provided in the detector chamber 24 and the reflector chamber 26, (mounted at the opposite ends of the opacity chamber 16) so as to ensure that as the sample is admitted via the tubes 14a and 14b to the ends of the opacity chamber 16 that all of the sample will be directed towards the outlet port 18, rather than a portion entering the detector and reflector chambers 24 and 26 and clouding either the detector or reflectors with particulate and which would cause erroneous readings and a shifting of the zero level thereafter. Thus, via the present novel sample flow path and optics configuration, a longer opacity chamber 16 is achieved and which for the present embodiment is on the order of fourteen inches long so as to provide a stronger signal than otherwise obtained with the previously known opacity chambers of four to six inches in length.

It should be noted, too, that relative to the air flow within the opacity chamber 16, it is directed in a cylindrically symmetrical fashion due to the coaxial Tees 28 that are mounted at the ends of the opacity chamber and at the midpoint at the outlet port 18. Generally, the coaxial Tees 28 act to produce a cylindrically symmetrical air flow as the air traverses the corners so as to minimize air turbulence and thereby reduce noise that is otherwise generated by the light beam difraction in the opacity chamber 16. In particular, without using the coaxial Tees 28, it has been noted that the light beam may shift with air turbulance to the point where it does not or only partially strikes the detector 30 and which is centrally mounted at the end of the opacity chamber 16. The nonturbulent flow, on the other hand, does not affect or artificially shift the light relative to the detector 30.

Referring to FIGS. 3a and 3b, respective cross-sectional elevation and end views are shown of the present coaxial flow Tees 28. From FIG. 3a, it is to be noted that the flow Tee 28 is essentially comprised of an outside body member 32 having an approximate inside diameter at each of its openings of ⅝ inch. A short section of tubing 34 having a plurality of holes 35 bored therein is, in turn, mounted within the horizontal bore of the member 32 and spaced away from the inside walls thereof via a pair of ring-like spacers 36 that act to centrally position the spacer 34 relative to the horizontal bore of the member 32. Thus, as air is admitted via the port 38, it is caused to flow downwardly and through the holes 35 through the center mounted tubular spacer 34 and out the ends 40 and 42. However, because of the pressure differential in the opacity chamber 16, due to the pump 20, the exhaust sample air is caused to flow only out one of the side ports 40 or 42 of each of the cross Tees 28 mounted at the extreme ends of the opacity chamber 16, while a minimal amount of environmental air is admitted via the other port, as mentioned above via the orifices 22. Thus, as the air passes through the coaxial Tees 28, it is caused to enter and flow in the sample tube in a cylindrically symetric fashion as it passes towards the outlet port 18 and which swirling action does not affect the light source that passes through the center of the tubular spacer 34.

In FIG. 3b, the relative mounting of the spacers 36 and tube 34 can be more particularly seen relative to an end view of the cross Tee 28. From FIGS. 3a and 3b, it is to be noted that the spacers 36 are generally positioned equa-distant from one another at each of the ends of the coaxially mounted tube 34 so as to centrally mount the tube 34 within the horizontal bore of the cross Tee 28. For the ideal cross Tee 28, the spacers 36 and holes 35 should not affect the air flow. However, while some turbulence and noise is produced by the present cross tees 28, it has been found to be nominal relative to the amplified signal that is achieved with the longer optical chamber 16. In particular, the tolerance for the present equipment has been found to be on the order of only 0.02 percent over the duration of a typical test run. It should be noted, too, that the cross Tees 28 for the present equipment have typically been fabricated from stainless steel, copper or brass and to which the spacers 36 are separately affixed, although it may be preferable to fabricate the cross Tees 28 in a cast form. Also, and before referring to the optical portion of the present apparatus, it is to be noted that each of the input tube portions 14a and 14b and/or the opacity chamber 16 are heated via a resistance heater 44 that is wrapped around the tubes 14a and 14b and 16 so as to prevent against condensation forming in the input tubes and the opacity chamber 16.

Referring again to FIG. 2 and directing attention to the optical thereof, it is to be noted that they are essentially comprised of a pulsed light source 46 (which for the present embodiment is an appropriately controlled light emitting diode (LED)), a beam splitter 48, a plurality of apertured aluminum plates 50, a flat mirror 52, a concave mirror 53 and the detector 30. In operation, the light source 46 is operated at a ten kilohertz rate (well above the 60 hertz line noise) and a 50 percent duty cycle so as to generate a light source of a source wave length of 680 nanometers. The light is passed through a beam splitter 48, whereat approximately five to ten percent of the light is reflected onto a reference detector 54 so as to generate a reference signal by which the light source 46 is feedback controlled and whereby a constant zero base line is, in part, achieved. Upon passing through the beam splitter 48, the light passes through a plurality of black, aluminum plates 50 having apertures of approximately 1/16 inch in diameter formed therein for creating a collimated light beam which is reflected via flat mirror 52 and reflected and focused via the concave mirror 53 and redirected through the center of the opacity chamber 16. As the light beam traverses the opacity chamber 16, the light impinges upon the particulate containing air and which generates losses due to absorption and scattering and thus reduces the intensity of the light beam detected at the detector 30. The detected beam is, in turn, amplified, subtracted from the reference value from the detector 54 and displayed as a relative percentage value between the display extremes of zero and 100 percent opacity.

It should be noted too, that while noise may be interjected from a number of sources, the present apparatus seeks to minimize this noise in a number of ways. In particular, tolerances of 0.02 percent are achieved through the use of the coaxial flow Tees 28, the concave mirror 53 which focused the light beam, and the feedback coupling of the light detected by the reference detector 54 and which acts to stabilize the operation of the light source 46 so as to produce a relatively continuous and constant measure of light.

Relative to the reference detector 54, attention is also directed to FIG. 4 and wherein an alternative embodiment is shown for improving the relative operation between the reference detector 54 and the primary detector 30. In particular, the embodiment of FIG. 4 contemplates the mounting of the detectors 30 and 54 in the same thermal environment as by mounting both of the detectors on the same printed circuit board 56 and heat sink (not shown) so as to ensure that each tracks the ambient temperature in the same way. This is necessary because the sensitivity of each of the semiconductor detectors 30 and 54 is different when they are not exposed to the same ambient temperature conditions. For this embodiment, too, the reference detector 54 is mounted behind the light source 46 and thereby monitors the back scattered light, rather than the light reflected from a beam splitter 48. Further, the ends of the opacity chamber 16 are capped (although only one end is shown) with a clear transparent window 58 and an additional air inlet orifice 22 is bored in the side of the opacity chamber 16 so as to ensure against the previously described particulate buildup. For this embodiment, too, should some particulate in spite of the pressure differential flow towards the detector chamber 24 or reflector chamber 26, the particulate will collect on the window 58, in lieu of contaminating the detectors 30 and 54. Such a window 58 can, in turn, easily be cleaned on a regular basis so as to ensure proper equipment operation. Further, should the window 58 become clouded with time, this would be indicated to the operator via a rising zero reference.

Figures 5, 5A:
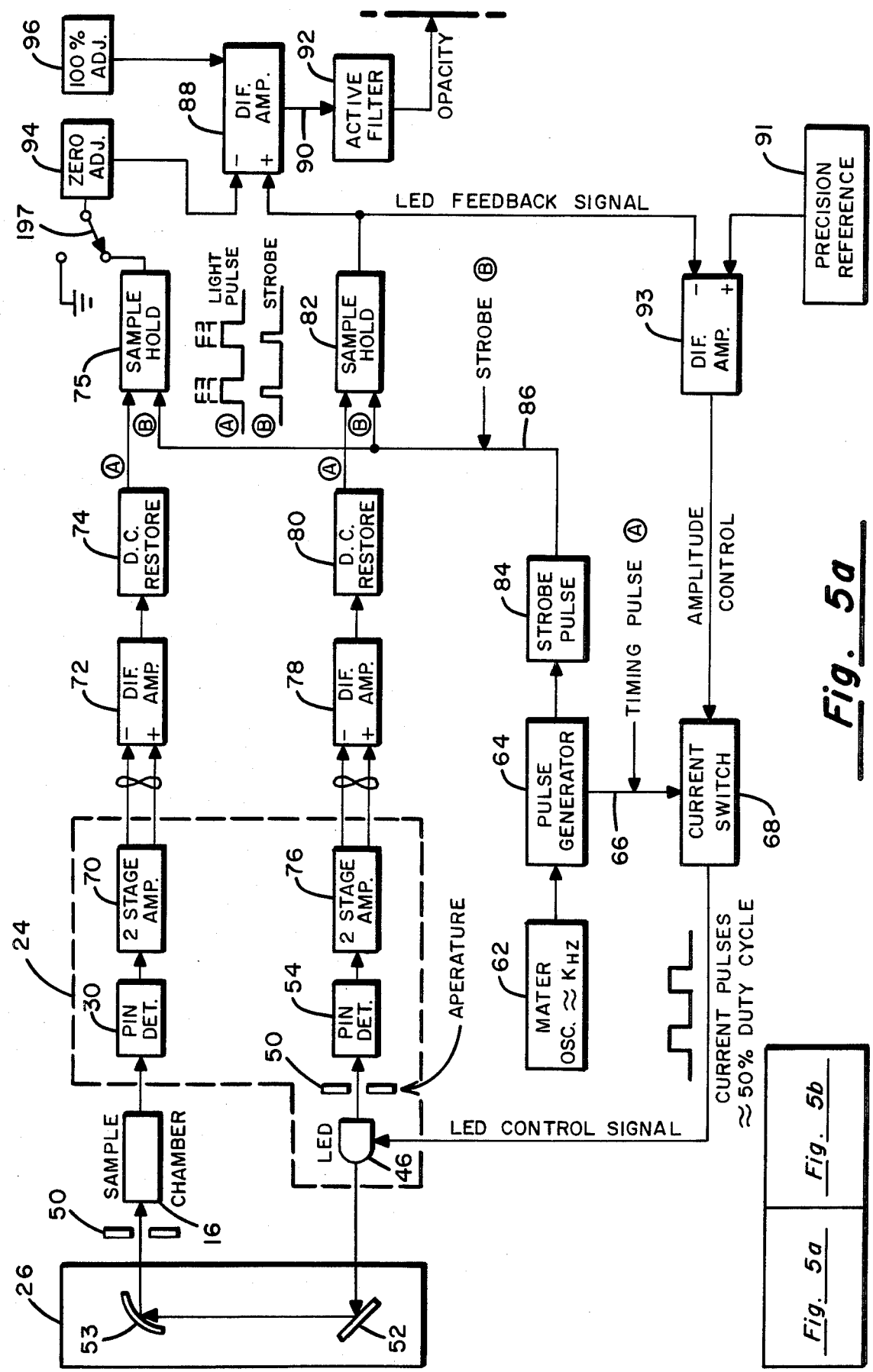
FIG. 5, comprised of FIGS. 5a and 5b, shows a detailed block diagram of the control circuitry for the present apparatus.
Figure 5B:
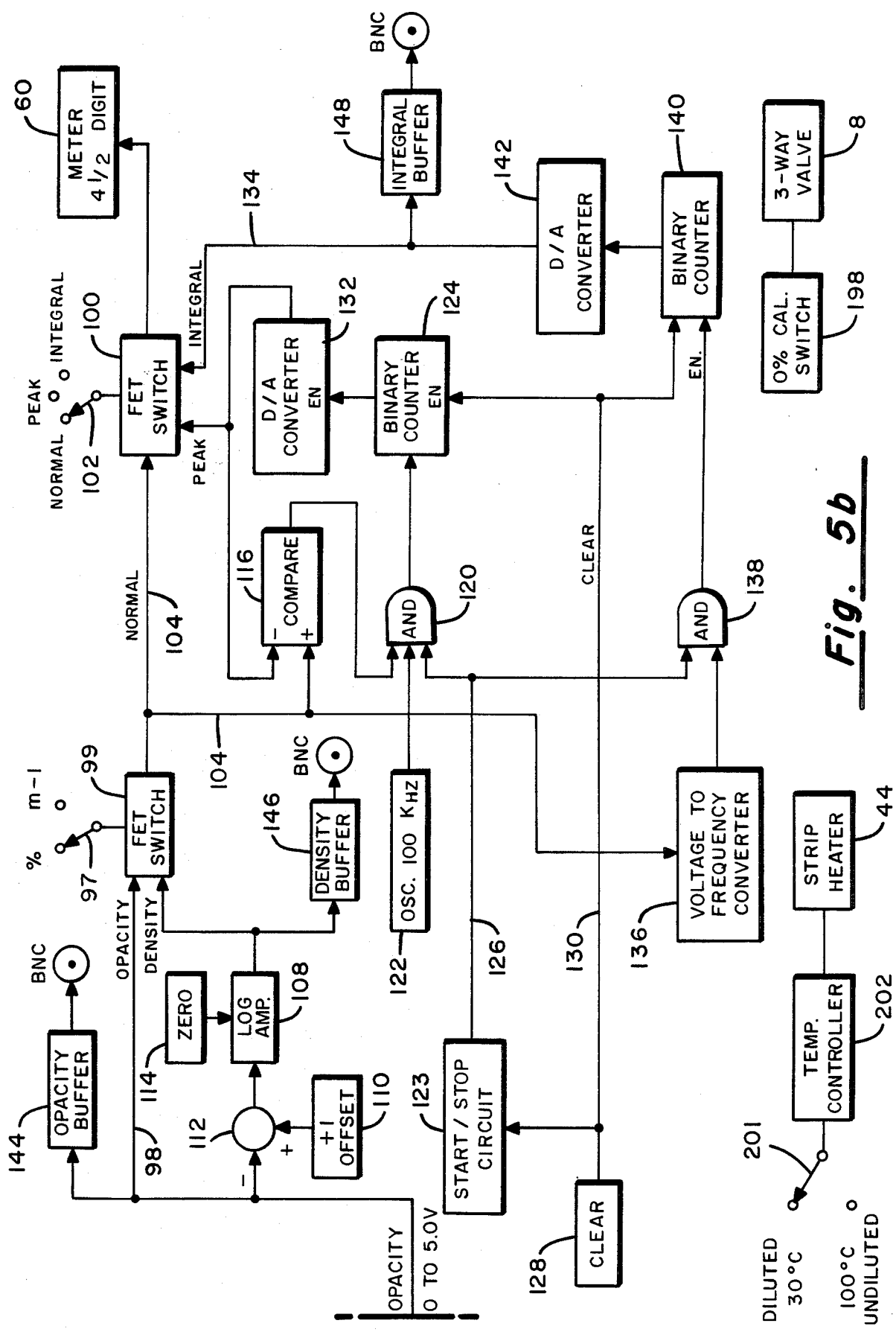

Referring now to FIG. 5, comprised of FIGS. 5a and 5b, a detailed block diagram is shown of the control circuitry for the present apparatus. From FIG. 5a, a generalized block diagram is shown of the light source generating and detecting circuitry and the light calibration circuitry. FIG. 5b, on the other hand, shows the circuitry relative to the measurement of the sample, opacity and density in three modes namely normal, peak hold and integral values relative to the digital display 60, shown at FIG. 1. Initially, through, attention is directed to FIG. 5a and which is shown relative to the alternative reference light arrangement of FIG. 4. From FIG. 5a, a master ten kilohertz crystal oscillator 62 is coupled to a pulse generator 64, that produces voltage pulses at a 50 percent duty cycle. These pulses are coupled via conductor 66 to current switch 68. The current switch 68, in turn, produces current pulses of approximately 200 milliamps peak value at a ten kilohertz rate and a 50 percent duty cycle and which output is used to the pulse LED light source 46. The thus generated light beam is then reflected by the flat mirror 52 and focused via the concave mirror 53 before passing through the sample chamber 16 and being detected at the PIN type diode or other similar detector 30. The light sensed at the detector 30 is next amplified via a two-stage amplifier 70 and an associated differential amplifier 72 before being AC coupled to a DC restore circuit 74. The DC restores circuit 74 comprises a precision clamp which maintains the base line or the most negative valve of pulse at exactly zero volts. The AC signal with the correct DC value restored thus comprises the light pulse signal A and which is then sent to the sample hold circuit 75. The sample hold circuit 75, in turn, produces a DC signal proportional to the peak AC value determined at the strobe time. This DC valve is then stored until the next strobe time.

As the LED 46 is pulsed, the back scattered light impinges upon the aperture containing plate 50 mounted there behind so as to cast light upon the reference detector 54. The detector 54, in turn, produces an analog reference signal (similar to the light pulse signal A) which is amplified via a two-stage amplifier 76 and an associated differential amplifier 78 before being subjected to its associated DC restore circuitry 80. A related reference peak-to-peak analog signal is generated via the DC restore circuitry 80 and stored within the sample and hold circuitry 82 in a similar fashion to that described above for the sample signal channel. The generated DC signals stored within the sample and hold circuits 75 and 82 are thus produced at the same rate at which the LED light source 46 is pulsed with each having a magnitude dependent upon the sensed levels.

At the same time, the pulse generator 64 applies its ten kilohertz output to the strobe pulse generator 84 and which acts to produce a shifted strobe signal (B) centered about the light pulses. Upon receipt of the strobe signals B via the conductor 86, the sample and hold circuits 75 and 82 sample the peak values of the AC signals which are sent to the amplifier 88 where the magnitude of the signal associated with the light sample from the opacity chamber 16 is subtracted from the light reference signal from the reference detector 54. Thus, the output of the differential amplifier 88 on conductor 90 is representative of the percentage of light that is blocked via the particulates contained in the sample. This opacity signal, and which is a value between 0 to 5.0 volts is next filtered via the active filter 92 before it is coupled to the various circuitry of FIG. 5b and which acts to measure and display normal, peak hold and integral values for the related opacity and density measurements.

Before referring thereto, however, it is to be noted that associated with the differential amplifier 88 are individual zero adjust and 100 percent adjust controls 94 and 96 and which act to appropriately bias the differential amplifier 88 relative to its low and high ends of operation. In particular, the zero adjust control 94 is used to adjust the output amplitude of the sample and hold circuitry 75 so that it exactly matches the reference amplitude of the sample and hold circuitry 82, when clean air is in the sampling chamber. The 100 percent adjust circuitry, on the other hand, controls the gain of differential amplifier 88 when the output of the sample and hold circuitry 75 is set to zero. This condition thus simulates 100 percent opacity. Assuming that the meter 2 has been adjusted, the filtered signal from the filter 92 thus comprises an analog signal indicative of the opacity for the sample under test and which signal has a relative value between zero to about five volts and which corresponds to the zero to 100 percent value at the display 60. Before continuing, it should also be noted, that the output of the sample and hold circuitry 82 is also compared to a precision reference signal 91 via differential amplifier 93. The output voltage of amplifier 93, in turn, is used to control the amplitude of the current pulses of the current switch 68. This voltage thus completes the LED feedback, which maintains an effective constant light beam (even though it is produced at a 50 percent duty cycle) as seen by the reference detector 54.

Because, too, opacity is exponentially related to density, the above obtained opacity value may also be processed so as to produce a relative figure of merit for the density of the particulates contained within the test chamber 16. Assuming for the moment though that opacity information only is desired and referring now to FIG. 5b, then in that event the toggle switch 97 associated with the field of effect transistor (FET) switch 99 is enabled to the percent (%) position and which causes the opacity value on conductor 98 to be selected and coupled to the FET switch 100. If the toggle switch 102 associated with the FET switch 100 is in its normal position, then the opacity value on conductor 104 will be switched via the switch 100 and coupled to the meter 60 where it will be directly displayed as a percentage value. Alternatively, the operator may set the switch 100 to the peak hold (Peak) position or the integral position and which will cause the respective maximum *peak* opacity value for the sample run to be displayed or the integral opacity for the entire run to be displayed. The details of the operation of the circuitry in these regards will be discussed hereinafter.

On the other hand, if the operator desires information relative to the density of the sample, then the toggle switch 99 is switched to the inverse mass ($M^{-1}$) position and whereat the density input to the FET switch 99 is selected. In that regards, the density input comprises the logrithmic value of the detected opacity and which is obtained from the logrithmic amplifier 108, due to the exponential relationship between density and opacity. Specifically, the analog opacity value is subtracted from a (+1) offset value or scale factor via the offset circuit 110 at the operational amplifier 112 before being logrithmically amplified via the amplifier 108 and which is biased via zero bias circuitry 114. The logrithmic value is then coupled via the switch 97 to the display 60, if the normal position is selected, or to further circuitry whereat either the peak value of the density signal is coupled via the switch 100 to the meter 60 or the integral thereof is selected.

Assuming for the moment though that the peak value has been selected for either the opacity or density signal, then the related analog opacity or density signal on conductor 104 is coupled to the comparator 116 which gates the output of a 100 kilohertz oscillator 122 to a binary counter 124. Thus, assuming the density input signal on conductor 104 exceeds the previous peak signal at the 100 kilohertz sampling rate, AND gate 120 produces an output and clocks the binary counter 124. At this point, it should be noted, too, that upon powering up the circuitry, via the enabling of the start/stop switch 123, AND gate 120 is enabled via an associated logic input from the start/stop circuitry 123 on conductor 126. Additionally, the counter 124 will have been cleared via an appropriate clear and enable signal from the clear circuitry 128 on conductor 130. Thus, if the input signal exceeds the feedback signal, the input from and gate 120 causes the counter 124 to count and which count is successively updated each time the input density exceeds the feedback signal. The count value is, in turn, coupled to the digital to analog convertor 132 and which acts to convert the accumulated count value to the equivalent maximum peak analog signal sampled up to that time and which is coupled to the FET switch 100 as well as to the comparator 116. From the switch 100, the peak signal is, in turn, coupled to and displayed at the digital meter 60 as the Peak Hold value for either the selected opacity or mass density. The Peak Hold value displayed thus reflects the maximum peak magnitude sensed for the analog signal for the sampling period and which peak value is incremented only via the comparator 116. This value is then continuously displayed, until it is cleared by the operator.

Should the operator, on the other hand, desire to know the integrated opacity or integrated density of the particulate containing exhaust that is being sampled, the switch 102 is toggled to its integrate position and which enables the FET switch 100 so as to couple the integral value on conductor 134 to meter 60. The integral of the opacity or density input is obtained via the voltage-to-frequency convertor 136 and which responsively produces a frequency at a rate dependent upon the level of the analog signal on conductor 104 and which dependent frequency signal is coupled via the AND gate 138 to a binary counter 140. The up counter 140, in turn, monitors the output from AND gate 138 and appropriately counts up so as to contain a value indicative of the total content of the particulate passing through the sample chamber 16. The value in counter 140 is, in turn, monitored via the digital-to-analog convertor 142 and the output of which is coupled via the FET switch 100 to the meter 60, where it is displayed. In passing it should be noted, too, that the digital integrator circuitry provides a stable signal over a long run time (over one hour) without the inherent zero drift problems that occur in conventional integrators.

Parenthetically, it should be noted that FIG. 5b also shows the temperature control circuitry comprised of two-position switch 201 and controller 202 for controlling the power supplied to strip heater 44. As mentioned, the heater 44 acts to heat the deliver paths 14a and 14b and the sample chamber 16 so as to prevent against condensation; the specific temperature selected depending upon whether heated exhaust gases are being tested or ambient air. Still further, the zero percent calibration switch 198 is shown relative to its control of the three-way valve 8 and which, as mentioned, is used during the initial calibration of the display 60.

Thus the circuitry of FIG. 5b permits the operator to variously display the analog opacity signal produced via the circuitry of FIG. 5a either in terms of opacity or density and in terms of either a normal, peak or integrated signal. In passing, it should also be noted that an opacity buffer amplifier 144, a density buffer amplifier 146 and a integral buffer amplifier 148 are also appropriately coupled to the present circuitry so as to permit the operator to couple appropriate recording equipment (i.e. a computer, strip chart recorder et al) to the circuitry so as to monitor the associated signals, and permit further processing or provide a permanent record of the test sample.

While the present particulate detecting apparatus has been described in detail with respect to its presently preferred embodiment, it should be apparent from the foregoing that various modifications may be made thereto without departing from the spirit and scope of the present invention. Accordingly, it is contemplated that the following claims shall be interpreted so as to include all those equivalent embodiments within the spirit and scope hereof.

What is claimed is:

1. Apparatus for measuring the particulate content of air comprising:
    an elongated hollow chamber having at least one end mounted input port and at least one output port mounted along the length of said chamber;
    means for coupling sample quantities of particulate containing air to said input port;
    light source means for directing a beam of light from one end through said chamber and the air therein;
    light detector means mounted along said chamber beyond said outlet port in opposed relation to said light source means for detecting emanating light;
    means for establishing a pressure differential from said input port to said output port and directing air flow towards said output port and away from said light source means and said light detector means; and
    means responsive to detected light for measuring the particulate content of the sample air.

2. Apparatus as set forth in claim 1 including means responsive to emitted light from said light source means for producing a reference light signal and wherein said measuring means includes means for subtracting said detected light from reference light signal.

3. Apparatus as set forth in claim 2 wherein said light detector means and said reference light means are mounted such that they are exposed to the same operating temperatures.

4. Apparatus as set forth in claim 1 including means for cylindrically symmetrically directing the sample air flow through said chamber, thereby minimizing air turbulence within said chamber.

5. Apparatus as set forth in claim 1 wherein said light detector means is mounted at an end of said chamber and each of said light source and said light detector means include means for admitting atmospheric air to the ends of said chamber.

6. A photo-optic system for measuring the particulate content of air, comprising:
    means for coupling samples of particulate containing air to said system;
    a sample chamber having first and second inlet ports for receiving said particulate containing air samples;
    an outlet port mounted along said sample chamber between said first and second inlet ports and coupled to means for drawing the said sample air towards said outlet port;
    light source means open to the atmosphere and coupled to one end of said sample chamber for directing a collimated beam of light through said sample chamber and including means for detecting a portion of said light beam and producing a reference light signal;
    light detector means open to the atmosphere and mounted at an end of said sample chamber opposite to said light source means for producing a signal proportional to the amount of light emanating from said chamber relative to said reference light signal; and
    means responsive to said proportional signal over a sampling period for selectively determining either a normal opacity value, a value corresponding to the peak magnitude of the sensed opacity or an integrated opacity value, wherein the peak value is determined by means for continuously comparing and counting at a first clock rate each instance where the magnitude of said sensed signal for one clock cycle exceeds the magnitude of the previous clock cycle, and wherein the integrated value is determined by means for converting said sensed signal to a corresponding frequency and for continuously counting the frequency dependent signal and thereby the total particulate detected for the sampling period.

7. Apparatus as set forth in claim 6 including flow shaping means for inducing non-turbulent air flow through said sample chamber.

8. Apparatus as set forth in claim 7 wherein said flow shaping means comprises a plurality of T-shaped hollow cylindrical members having horizontal and vertical flow portions, one of said T-shaped members being mounted at each of said inlet and outlet ports, and wherein each T-shaped member contains a tubular member mounted in concentrically disposed relation within the horizontal flow portion thereof and in flow communication through a plurality of holes through the wall of said tubular member with the vertical flow portion thereof, whereby air flow through each of said horizontal and vertical flow portions occurs as a cylindrically symmetrical column of air.

9. Apparatus as set forth in claim 6 wherein said light detector means and said light source means are maintained at the same operating temperature.

10. Apparatus as set forth in claim 6 including means responsive to said proportional signal for measuring the relative density of the particulates in an air sample as either a normal, peak or integrated density value.

11. Apparatus as set forth in claim 6 wherein said light source means includes a first flat mirror, a second concave mirror and a plurality of aperture containing members and wherein the light is directed through ones of the apertures to impinge on and be reflected by said flat mirror into said concave mirror and thence be focused and passed through said sample chamber and others of said apertures to said light detector means.

12. Apparatus as set forth in claim 6 including means for heating the walls of said sample chamber.

* * * * *